United States Patent [19]

Smith et al.

[11] 4,119,193
[45] Oct. 10, 1978

[54] SHUTTLE TYPE LIVESTOCK FEEDER

[75] Inventors: Kenneth L. Smith; Ernest H. Sancken, both of Eureka, Ill.

[73] Assignee: A. O. Smith Harvestore Products, Inc., Arlington Heights, Ill.

[21] Appl. No.: 736,487

[22] Filed: Oct. 28, 1976

[51] Int. Cl.² ............................................. B65G 69/04
[52] U.S. Cl. ................................... 198/371; 119/52 B; 198/577; 198/631; 198/750; 214/16 R; 214/17 C
[58] Field of Search ............. 198/312, 369, 371, 485, 198/535, 536, 542, 544, 569, 574, 577, 585, 588, 594, 603, 606, 631, 750, 362, 366, 586; 119/52 B; 214/16 R, 17 C, 21; 74/665 R, 665 A, 665 B, 665 E, 679, 681

[56] References Cited

U.S. PATENT DOCUMENTS

| 859,595 | 7/1907 | Camp | 198/371 |
|---|---|---|---|
| 2,834,484 | 5/1958 | De Vaney et al. | 198/631 |
| 3,063,582 | 11/1962 | Steffensen | 198/631 |
| 3,149,734 | 9/1964 | Ilmoni | 198/574 |
| 3,221,905 | 12/1965 | Storm et al. | 198/547 |
| 3,274,845 | 9/1966 | Moran, Sr. | 74/679 |
| 3,428,027 | 2/1969 | Haen et al. | 119/52 B |
| 3,530,973 | 9/1970 | Rossi | 198/577 |
| 3,554,355 | 1/1971 | Berg | 119/52 B |
| 3,570,650 | 3/1971 | Parsons | 214/17 C |
| 3,625,184 | 12/1971 | Patz | 119/52 B |
| 3,675,758 | 7/1972 | Buschbom et al. | 198/631 |
| 3,695,415 | 10/1972 | Bakker et al. | 198/547 |
| 3,929,219 | 12/1975 | Malcolm | 198/574 |

FOREIGN PATENT DOCUMENTS

1,281,946   10/1968   Fed. Rep. of Germany ........... 198/574

*Primary Examiner*—Bruce H. Stoner, Jr.
*Assistant Examiner*—Richard K. Thomson
*Attorney, Agent, or Firm*—Andrus, Sceales, Starke & Sawall

[57] ABSTRACT

A livestock feeder device having a reciprocating carriage or shuttle adapted to be driven back and forth over a receiver such as a feed bunk having one or more zones. An endless conveyor belt extends around spaced guides on the carriage. A belt drive mechanism is fixedly mounted separate from the carriage and selectively drives the belt continuously in either direction no matter which direction the carriage is moving, or even if the carriage is stationary. Feed discharge is made from either end of the belt, independent of the carriage drive. The latter drive includes mechanism for selectively determining the zone or zones into which feed is delivered.

2 Claims, 13 Drawing Figures

SHUTTLE TYPE LIVESTOCK FEEDER

BACKGROUND AND SUMMARY OF THE INVENTION

This invention relates to livestock feeders and the like, and more particularly to devices of the shuttle type for selectively distributing feed or other material along an elongated bunk containing one or more feed lots or zones.

In recent years, various improvements over the old belt, chain and screw type feeder conveyors have been made. One such improvement has been the shuttle conveyor, such as disclosed in U.S. Pat. No. 3,695,415 issued on Oct. 3, 1972 to Donovon L. Bakker et al and entitled "Feeder for Livestock." In that patent, a reciprocating carriage includes a pair of spaced rollers around which passes a conveyor belt. The belt is anchored so that as the carriage moves, the belt travels across the carriage and dumps feed off one of its ends into a bunk.

Previous shuttle conveyors for feeders, such as disclosed in the aforementioned patent, have been subject to certain disadvantages. Most importantly, these conveyors require that the carriage be moving in order for the belt to function to deliver the feed. Thus, it is not possible to continuously dump feed at a particular location, since the belt ends must always be moving longitudinally during discharge. In addition, the direction of carriage movement dictates the end of the belt from which feed is discharged, there being no possibility of changing carriage direction without changing the discharge end, or vice versa. The prior system has thus been limited in its flexibility of operation.

The present invention eliminates the aformentioned difficulties, while retaining the advantages of the shuttle type feed delivery system.

In accordance with the invention, and instead of anchoring the belt, the belt forms a continuous loop around the carriage idler pulleys, and is selectively and continuously driven from a reversible power driving mechanism fixedly mounted separate from the shuttle carriage. Feed is delivered from an input hopper continuously to one end of the conveyor belt, regardless of the direction of travel of the carriage. The delivery may be made to a feed receiving means such as another belt or to a discharge area or zone. Reversing of the conveyor belt drive provides continuous delivery to the opposite end.

A separate carriage drive, and controls therefor, selectively determines the zone or zones into which feed is delivered. The carriage may be parked at a desired location for continuous feed delivery to a receiving means such as a cross conveyor, a wagon or truck.

A motor may be used to drive the carriage and another to drive the belt, or a single motor may be employed to drive the carriage and belt independently of each other.

BRIEF DESCRIPTION OF THE DRAWINGS

The accompanying drawings illustrate the best mode presently contemplated by the inventors for carrying out the invention.

In the drawings.

DESCRIPTION OF THE PREFERRED EMBODIMENT

As best shown in FIGS. 1-5 of the drawings, the concept of the invention is embodied in a livestock feeder having an elongated feeding course comprising a trough or bunk 1 which may be mounted adjacent the ground. Bunk 1 is shown as having a plurality of partitions 2 which divide the bunk into a plurality of zones or receiving members 3. Six zones are shown and are further identified as L3a, L3a and L3c for the zones to the left of the midpoint of the feeder in FIG. 1; and R3a, R3b and R3c for the zones to the right of the midpoint of the feeder in FIG. 1. In some instances, the entire bunk may comprise only a single compartment or zone.

Figure 1:
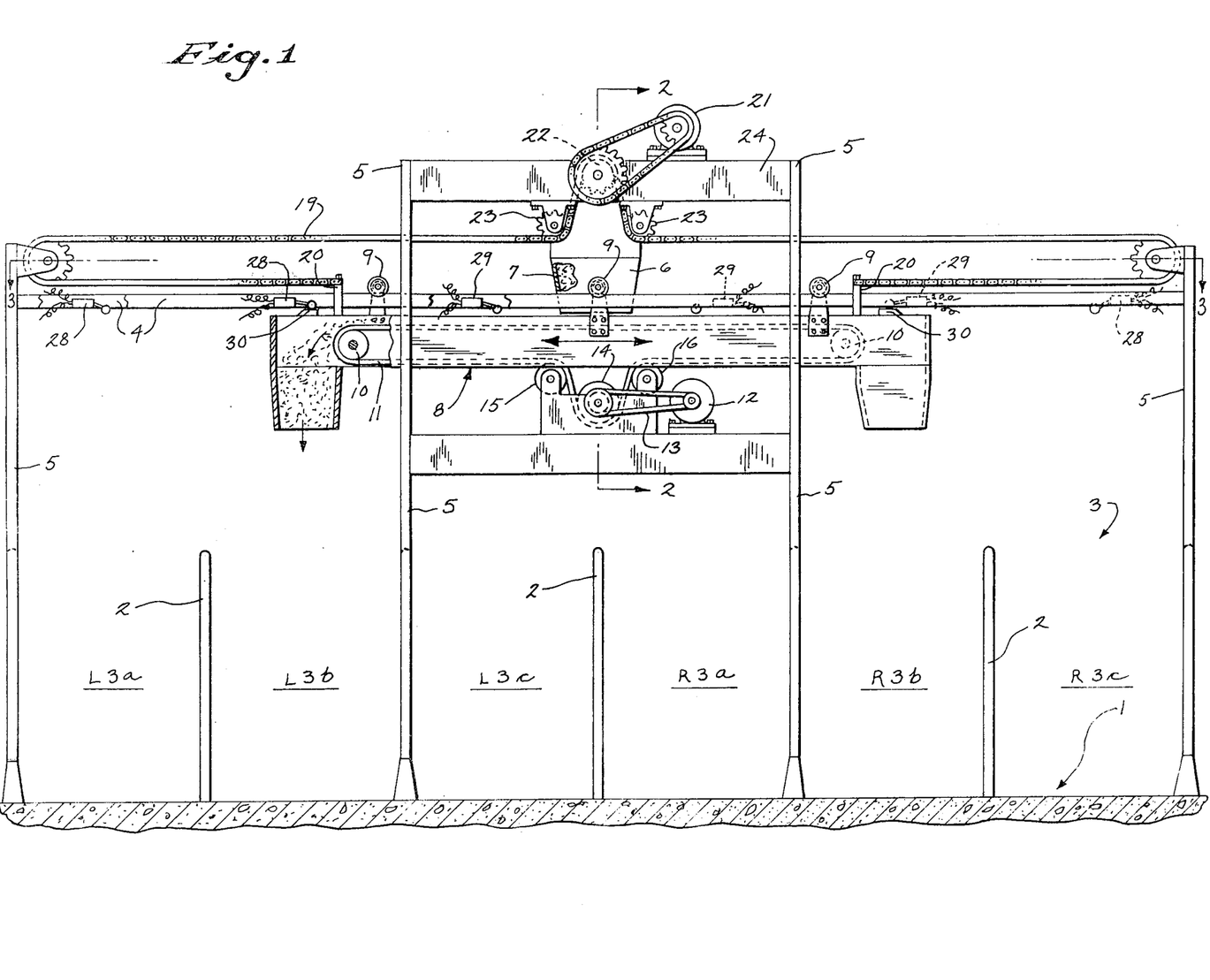
FIG. 1 is a somewhat schematic side elevation of a shuttle type livestock feeder constructed in accordance with the invention.
Figure 2:
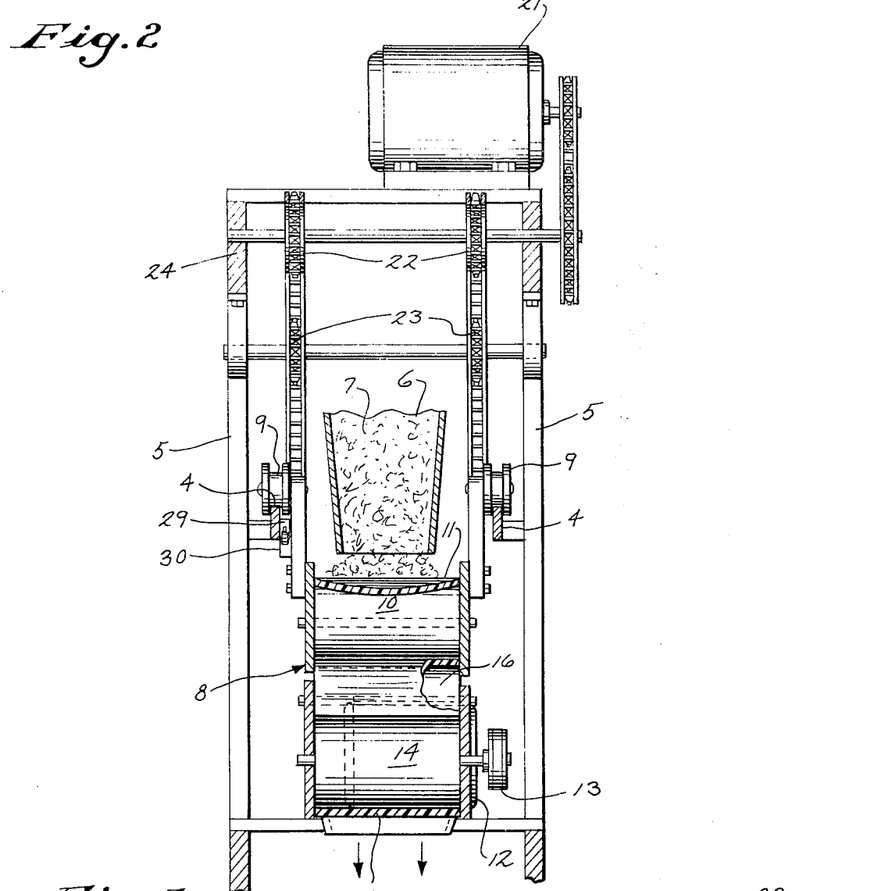
FIG. 2 is a transverse section taken on line 2—2 of FIG. 1.
Figure 3:
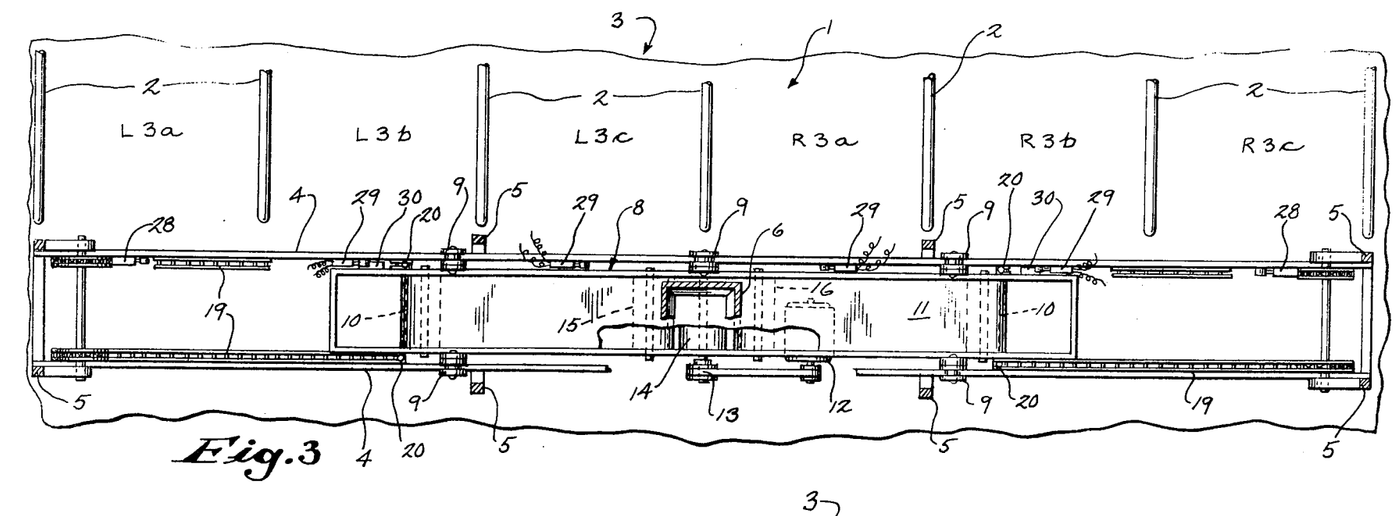
FIG. 3 is a fragmentary top plan view of a portion of the feeder taken on line 3—3 of FIG. 1.

A shuttle zone type feeding apparatus runs the length of bunk 1 to deliver feed to one or more zones as desired. For this purpose, an elongated track 4 is disposed above and coextensive with bunk 1 and is held in place by suitable framework supports 5. A source of feed, such as a supply hopper 6, is disposed above track 4 midway of its ends for downward discharge of feed 7.

An elongated carriage 8 extends longitudinally along track 4 and is mounted for shuttling movement therealong, as by suitable wheels 9. Carriage 8 carries conveyor means which receives feed from hopper 6 and delivers it to bunk 1. For this purpose each end of the carriage is provided with guide means, such as idler rollers 10 which are located inside the carriage and adjacent each discharge end of carriage 8. A flexible conveyor belt 11 extends along the top of the carriage and passes downwardly and inwardly around idler rollers 10.

In accordance with the invention, belt 11 forms an endless loop which is continuously driven by means independent of the means for the movement of carriage 8. The drive means shown comprises a stationary motor 12 which is fixedly mounted, as to a support 5 beneath track 4, although motor 12 could be attached to carriage 8 and move with it. The output of motor 12 is connected via a suitable reduction drive and a belt 13 to a drive roll 14. A pair of snubber rolls 15 and 16 are disposed on each side of roll 14. Rolls 14, 15 and 16 are also fixedly mounted, as to support 5, beneath the midsection of track 4 and thus beneath hopper 6. Conveyor belt 11 extends beneath carriage 8, passes over snubber rolls 15, 16 and beneath drive roll 14. Alternately drive roll 14 may be located above snubber rolls 15 and 16 so that belt 11 can pass under snubbers 15 and 16 and thence over drive roll 14.

Figure 5:
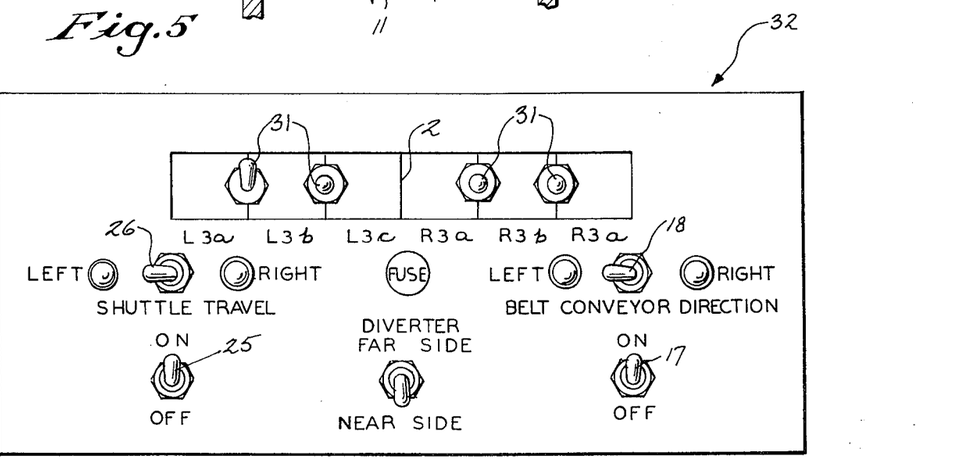
FIG. 5 is a view of a control panel for the carriage drive and conveyor means drive.

Motor 12 is reversible and is shown as being controlled by an actuating on-off switch 17 and a reversing switch 18 indicating left or right direction of feed discharge. Thus, selective operation of motor 12 will cause the top member of belt 11 to move transversely between hopper 6 and the drive belt and convey feed received from central hopper 6 to either the left or right end of carriage 8, where the feed will drop down into bunk 1. The conveying operation is continuous, regardless of the position of the carriage, or whether or not the carriage is moving.

In view of the fact that hopper 6 discharges onto the elongated upper surface of conveyor belt 11 centrally of track 4, carriage 8 need only be one-half the length of the track.

For purposes of delivering feed 7 to a selected zone of bunk 1, means are provided to shuttle carriage 8 back and forth between the ends of track 4, and between and within the respective zones 3. Drive chains extend longitudinally and co-extensively along carriage 8 and are secured at their ends to carriage brackets 20. A single drive chain and bracket at each end could be employed. The output of a carriage drive motor 21 is connected to drive a suitable sprocket 22 over which chain 19 extends. Snubbers 23 may also be utilized. Motor 21, sprocket 22 and snubbers 23 are fixedly mounted separate from carriage 8, as on a frame 24 which is supported by means of supports 5.

Carriage drive motor 21 is reversible and is shown as being controlled by an activating on-off switch 25 and a reversing switch 26 indicating left or right carriage movement. Thus, selective operation of motor 21 will cause carriage 8 to either remain stationary or to move longitudinally in either direction along track 4.

Even though carriage 8 may remain stationary, feed may be continuously fed onto belt 11 and delivered at a fixed location at one or the other of the belt conveyor ends.

Figure 4:
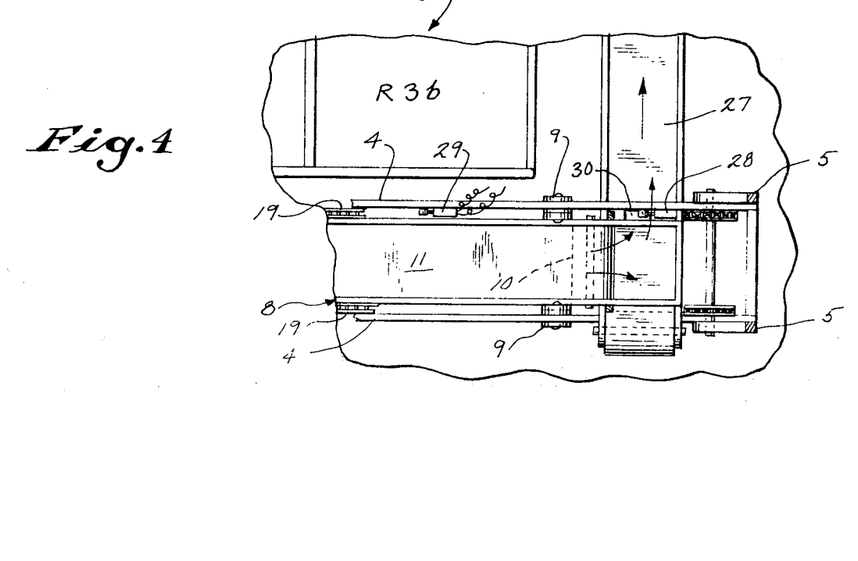
FIG. 4 is a fragmentary view of the right hand end of a slightly modified feeder having a cross-conveyor.

FIG. 4 illustrates a feeder system which includes, instead of the right end bunk zone R3c, a cross conveyor 27 which can receive feed discharged from belt 11 and transport it to any suitable place, such as another shuttle feeder, not shown. In this instance, carriage motor 21 is actuated to move carriage 8 until the right end of belt 11 is over conveyor 27. The motor is then stopped to park carriage 8. Actuation of belt motor 12 will cause discharge of feed onto conveyor 27.

Suitable limit switches 28 may be placed at the ends of track 4 and similar programming switches 29 may be placed corresponding to each bunk zone. Switches 28 and 29 are adapted to be selectively actuated by cams 30 positioned along carriage 8 at positions which correspond to the stalls between the various partitions 2. The switches are connected to carriage drive motor 21 in the conventional way, and when actuated by engagement of a cam 30, will automatically reverse the motor and carriage direction. The switches may be selectively operated by toggle switches 31 on a control panel 32 (FIG. 5) having a layout thereon similar to the bunk and showing the respective zones L3a, L3b, L3c, R3a, R3b and R3c. The switches 31 correspond to the placement of the programming switches 29. No programming switch 29 is needed for the center partition 2 because end limit switches 28 will control the carriage movement.

By selecting one or more of programming switches 29, carriage 8 can be caused to automatically reciprocate back and forth between the end boundaries of any single zone or group of adjacent zones.

If carriage 8 is shifted when belt 11 is not being driven, the carriage will move beneath the belt and thus progressively expose different belt portions at the top thereof.

In addition to a shuttle type feeder such as that shown and described in FIGS. 1-5, which is fed from the center and free to travel left and right, several shuttles of the same type can be paired together in a cascading arrangement. If it is assumed that the first shuttle, as shown in FIGS. 1-5, is 125 feet in length and, therefore, designed to reciprocate, for example, over an area of 250 feet, a corresponding second 125 foot shuttle can be paired with the first shuttle to cover a feeding area together of 250 feet to the left and 250 feet to the right. By feeding from a center hopper onto the first shuttle and then to the second shuttle, with the shuttles moving to both the left and right, as shown in FIGS. 6a-6d, a total feeding capability of 500 feet can be provided. This is illustrated diagrammatically in FIGS. 6a-6d.

Figure 6A:
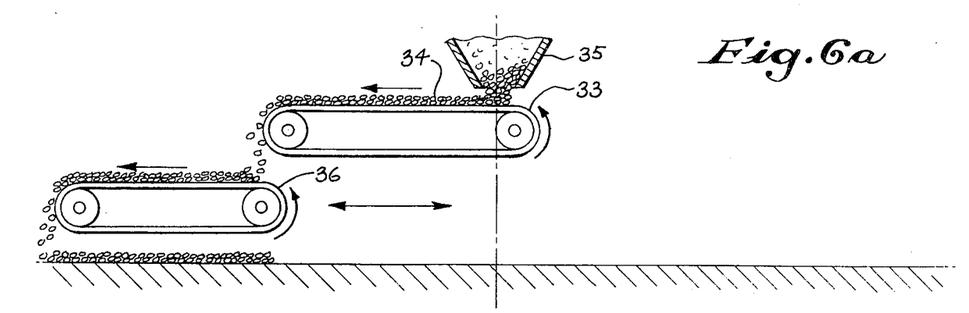
FIGS. 6a-6d diagrammatically illustrate the combination of a pair of livestock feeders of the invention arranged to discharge feed in a wider range of feeding area.

As shown in FIG. 6a, the first shuttle 33 corresponding to that of carriage 8 and conveyor belt 11 described with reference to FIGS. 1-5 is moved to the extreme left limit of its travel where the carriage is stopped while the belt continues to run and receive feed 34 from hopper 35 and deposit it on the second shuttle 36 which is shown as moving to the left and discharging feed 34 into a feed receiving member or feed zone, not shown.

Figure 6B:
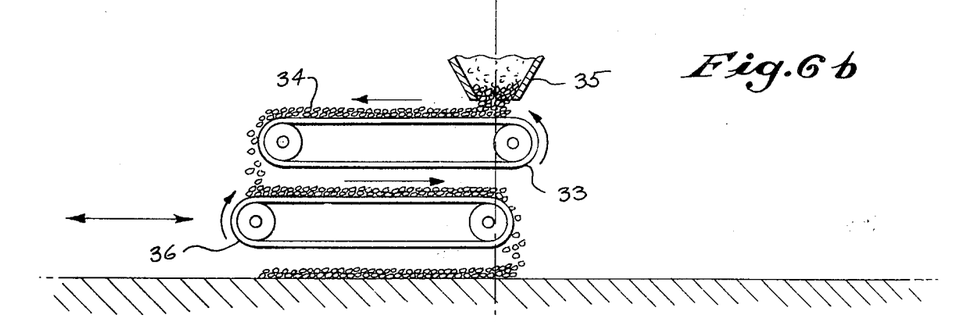
Figure 6C:
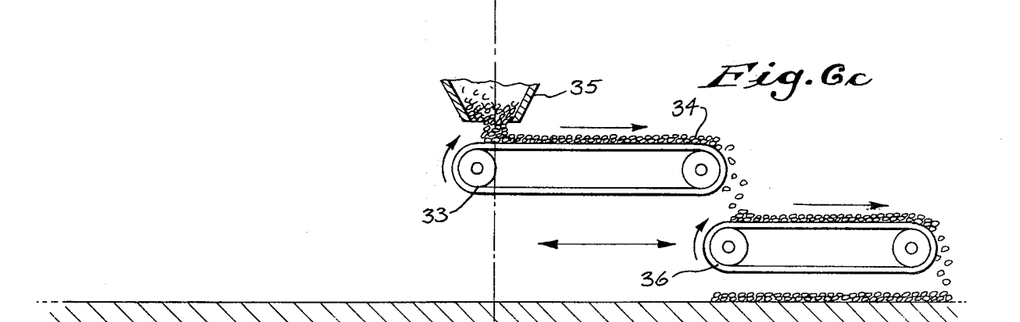
Figure 6D:
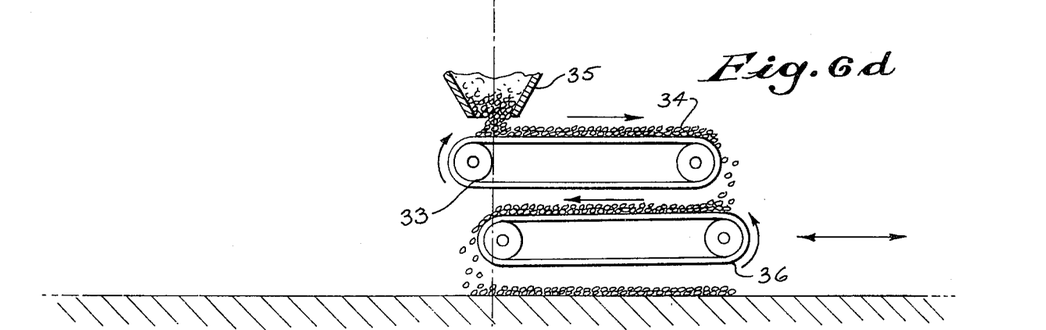

Shuttle 36 then reverses direction, as shown in FIG. 6b, while continuing to receive feed from shuttle 33 and discharging the feed into a receiving member of feed zone, not shown. FIGS. 6a and 6b illustrate the reciprocating motion of shuttle 36 below the discharge end of shuttle 33. As next observed in FIG. 6c, shuttle 33 has been moved to the extreme right limit of its travel where the carriage is stopped and the belt continues to run and receive feed 34 from hopper 35 and deposit it on shuttle 36 from which it is discharged. Shuttle 36 reversed direction as shown in FIG. 6d while still receiving and discharging feed 34. FIGS. 6c and 6d illustrate the reciprocating motion of shuttle 36 below the discharge end of shuttle 33.

The overall operation in pairing the shuttles 33 and 36 under the described example of each shuttle being 125 feet in length covers a feed discharge area of 500 feet. Different lengths of feed discharge can be obtained by different length or numbers of shuttles and reciprocal movement of the same.

Under another embodiment of the invention, a single drive motor is used to drive the carriage and the endless conveyor belt.

Figure 7:
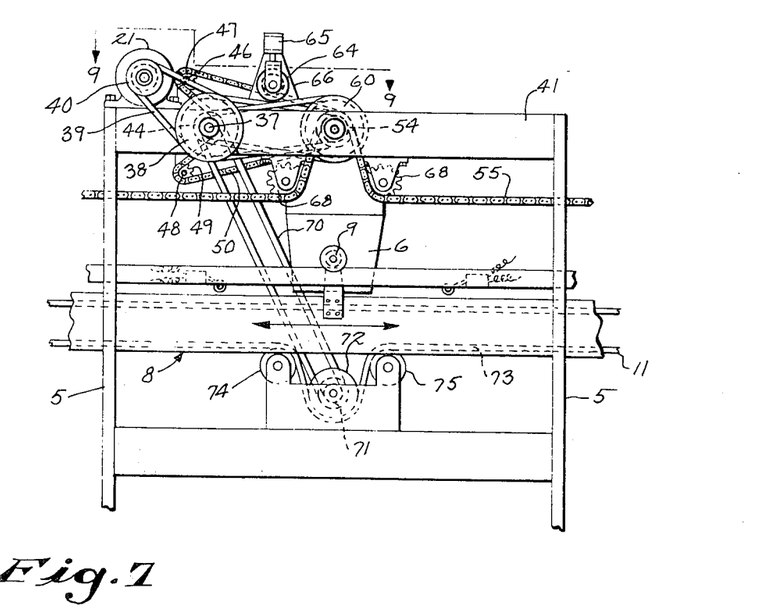
FIG. 7 is a front elevational view of the driving arrangement for the feeder utilizing only one motor.
Figure 8:
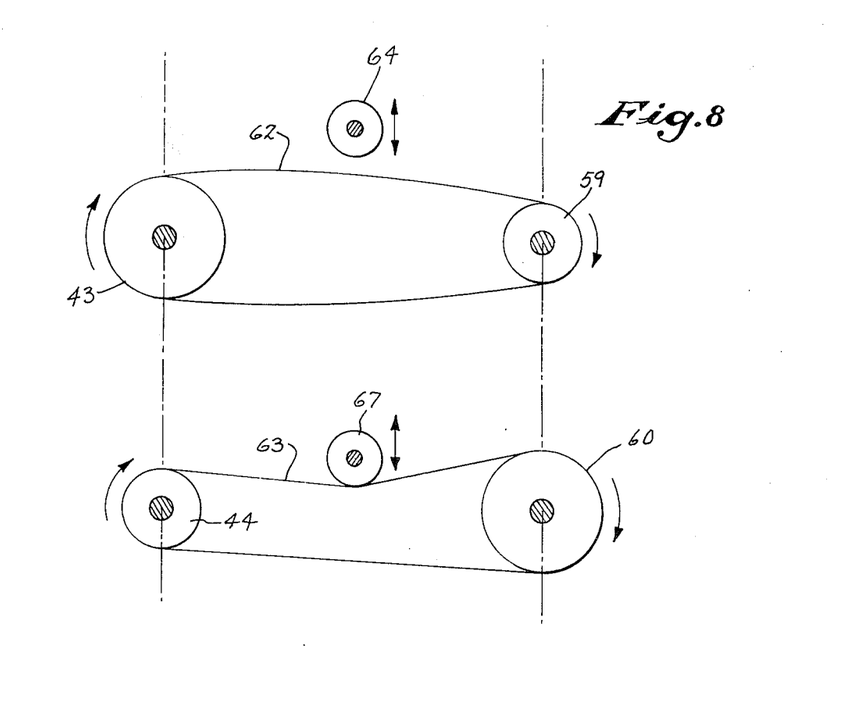
FIG. 8 is a diagrammatic view illustrating the belt drive of the shuttle carriage shaft.
Figure 9:
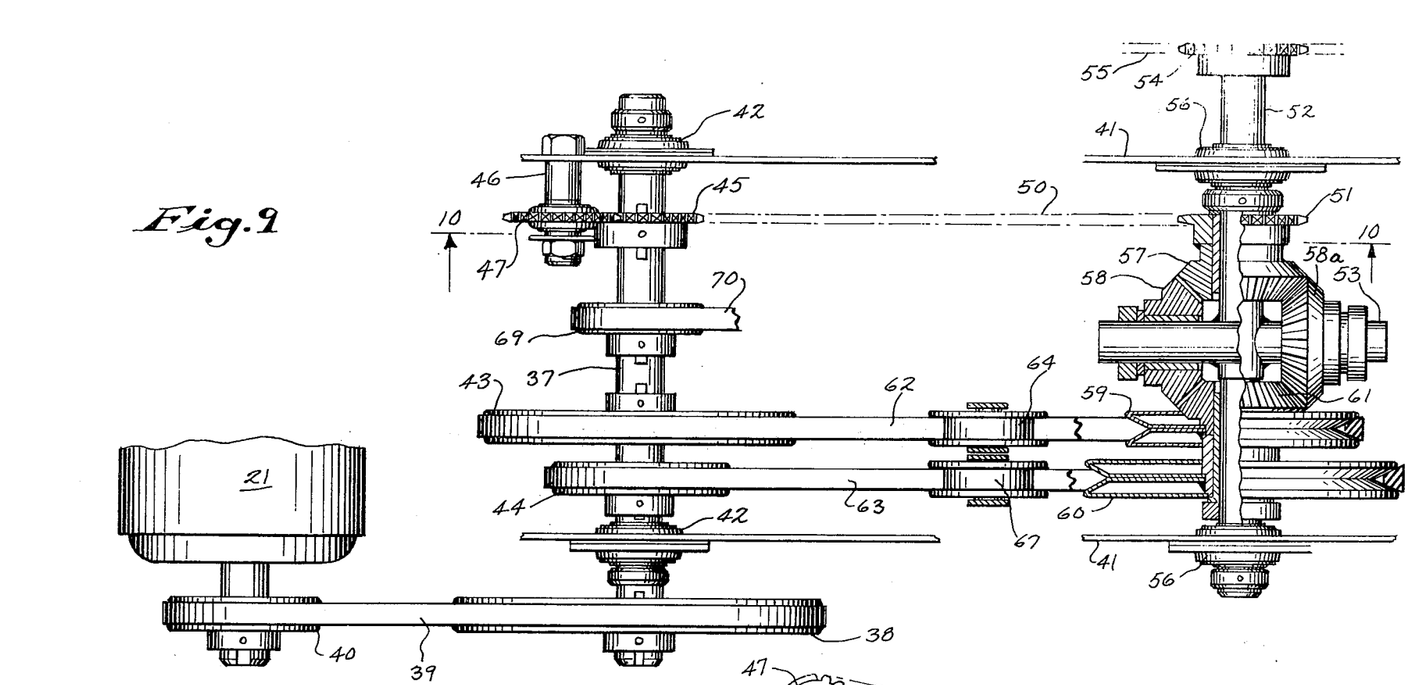
FIG. 9 is a section taken on line 9—9 of FIG. 7.

As illustrated in FIGS. 7-10 of the drawings, the motor 12 would be eliminated and the motor 21 of the first embodiment would drive the shaft 37 at a constant rpm by the pulley 38 through belt 39 connected to a drive pulley 40 on motor 21, as shown in FIG. 9. Pulley 38 is suitably connected to shaft 37.

The shaft 37 is supported within the frame 41 by the bearings 42 located at opposite end portions of shaft 37. A large pulley 43 and small pulley 44 are keyed in spaced relation to shaft 37 adjacent the bearing 42 at the input end of shaft 37 and are driven by shaft 37 such as in a clockwise direction.

At the end of shaft 37 opposite the input end, a drive sprocket 45 is keyed to shaft 37 to be rotated thereby. A stub shaft 46 is bolted to frame 41 and supports the idler sprocket 47. As may be observed in the detailed illustration in FIGS. 7 and 10, a second stub shaft 48 secured to frame 41 supports a second idler sprocket 49 beneath and generally in line with idler sprocket 47.

Figure 10:
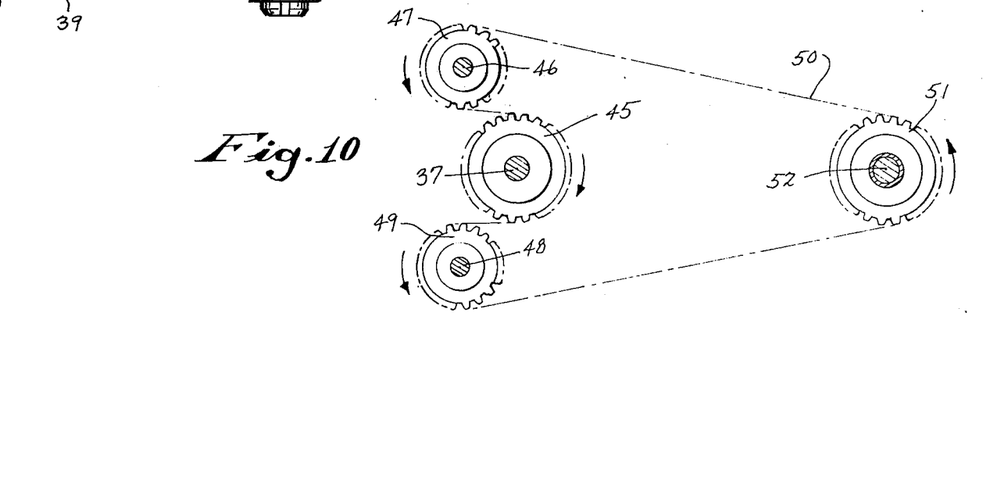
FIG. 10 is a section taken on line 10—10 of FIG. 9.

The endless chain 50 passes over the idler sprockets 47 and then forwardly over the forward side of drive sprocket 45 and thereafter reverses to pass over the lower idler sprocket 49. Endless chain 50 then passes around the sprocket 51 on output shaft 52. The two idler sprockets 47 and 49 are employed in connection with chain 50 so that sprocket 45 and sprocket 51 can be rotated in opposite directions as illustrated in FIG. 10 in which sprocket 45 is shown as rotated clockwise and sprocket 51 counterclockwise.

A basic part of the drive of carriage 8 is a miter gear differential with the cross shaft follower 53 which is secured to and drives the output shaft 52. Shaft 52 has a sprocket 54 keyed thereto for driving the carriage 8 through chain 55 in the desired direction. Output shaft 52 is rotated in bearings 56 located at opposite ends of shaft 52 in the frame 41.

The sprocket 51 which rotates freely on shaft 52 upon rotation in turn rotates miter gear 57 to which it is welded as shown in FIG. 9 of the drawing which rotates the cross shaft follower 53 through gear 58 and gear 58' secured to follower 53 to thereby drive the output shaft 52 such as in a counterclockwise direction. The output shaft 52 is driven in forward or reverse or clockwise or counterclockwise by follower 53 to drive shuttle carriage 9 in the desired direction. The reversible drive of output shaft 52 is accomplished without reversing the direction of the drive of the feeder conveyor 11.

The input by chain 50 to shaft 52 may be considered to be the primary input of the drive. The secondary input consists of the generally large pulley 43 and small pulley 44 which are keyed to the main drive shaft 37 and are aligned respectively with the small pulley 59 and the large pulley 60 on the output shaft 52.

The pulleys 59 and 60 are secured to miter gear 61 which is mounted for free rotation on shaft 52 and engages gear 58 on cross shaft follower 53 to thereby rotate cross shaft 53 and output shaft 52. Miter gear 61 will always rotate in the same direction as shaft 37.

The belt 62 on the pair of pulleys 43 and 59 and belt 63 on the pair of pulleys 44 and 60 are normally mounted loosely on the pulleys, as shown in FIG. 8, so that even though pulleys 43 and 44 are rotating, no power is transmitted to pulleys 59 and 60 from shaft 37 until belts 62 and 63 are tightened.

Referring to FIGS. 7 and 8, there is shown a movable idler pulley 64 which can be moved through linkage, not shown, manually or by the solenoid 65, as seen in FIG. 7, supported on bracket 66 into and out of engagement with belt 62 which encircles pulleys 43 and 59. A second idler pulley 67, which is shown diagrammatically, can be similarly placed in and out of engagement with the belt 63 which encircles pulleys 44 and 60. When the idler pulleys 64 and 67 engage the respective belts 62 and 63, this effects rotation of pulleys 59 and 60 and the output, miter gear 61, cross shaft follower 53, and output shaft 52 such as in a clockwise direction. One pair of the pulleys will provide a speed up drive and the other pair will provide a step down drive of shaft 52.

The result of the arrangement described is that when the belt 62, for example, is tightened by its respective idler pulley 64, miter gear 61 will rotate at a higher speed or greater rpm and opposite in direction from miter gear 57, thereby causing output shaft 52 to rotate in a clockwise direction. If belt 63 is tightened by idler pulley 67, miter gear 61 will rotae at a lower speed and opposite in direction from miter gear 57, thereby causing output shaft 52 to be rotated in a clockwise direction by the cross shaft follower 53. The belt drive ratios are selected so that the correct output shaft speed is obtained. Sprockets 45 and 51 are of the same size as shown in FIGS. 9 and 10 and as described the pulley 43 is larger than pulley 59 and pulley 44 is smaller than pulley 60. If the pulleys were of the same size such as sprockets 45 and 51, then shaft 52 would not be driven in either direction.

The primary and secondary drives of shaft 52 result in moving the shuttle carriage 8, as seen in FIG. 1, between the ends of track 4 and between and within the respective zones 3. The drive chain 19, as shown in FIG. 1 and seen in FIG. 7, extends longitudinally and is secured at its ends to carriage brackets 20. The output of shaft 52 is connected through sprocket 54 and chain 55 to drive carriage 8. Snubbers 68, as shown in FIG. 7, may also be utilized.

In order to drive the conveyor belt 11 continuously and independently of the drive of the carriage, a pulley 69 is keyed to the drive shaft 37. The belt 70 extends around pulley 69 and also around the pulley 71, as seen in FIG. 7. Pulley 71 in turn then drives the belt drive roll 72, as shown in FIG. 7, to drive the conveyor belt 73. The snubber rolls 74 and 75 may be disposed on either side of drive roll 72.

The concept of the present invention provides a greater flexibility of shuttle feeding than previously known. The feed conveyor mounted on the reciprocal carriage operates independently of carriage movement and permits continuous feed discharge.

Various modes of carrying out the invention are contemplated as being within the scope of the following claims particularly pointing out and distinctly claiming the subject matter which is regarded as the invention.

We claim:

1. In a feeder for discharging feed into one or more feed receiving means of an elongated feeding course, the combination comprising an elongated track extending longitudinally along said course and co-extensive therewith, a carriage mounted for travel along said track, drive means for reciprocatingly moving said carriage on said track, a pair of guide means longitudinally spaced from each other and disposed at opposite ends inside of said carriage, an endless loop conveyor member having an elongated top portion extending between said guides for receiving feed and with said conveyor member extending downwardly around said guides and extending inwardly beneath the said top portion, independent means selectively reciprocating said conveyor member about said guides in the same or opposite direction of movement of the carriage to carry feed for discharge at an end of said top portion into one of said receiving means, and the receiving means being at least one or more corresponding feeders cascaded below the first feeder in which at least the first uppermost feeder and the second feeder located directly below the first feeder are initially moved longitudinally in the same direction with the second feeder running slightly ahead of the first feeder, an endless loop conveyor secured to the first feeder to receive and discharge feed, an endless loop conveyor secured to the second feeder and initially rotating in the same direction as the loop conveyor of the first feeder to receive and discharge feed therefrom received from the first feeder, the second feeder at the end of its run then reversing its direction of travel and the rotation of its loop conveyor, the first feeder thereafter reversing its direction of travel and the reciprocation of its loop conveyor as the second feeder commences to pass from below the first conveyor to thereby discharge feed to the second feeder as the feeders both travel longitudinally in a direction opposite to that of the starting travel of said feeders, and the second feeder then reversing direction to move to starting position with its endless loop conveyor reversing rotation to its initial rotating direction and then the first feeder reversing direction to move to its starting position with its endless loop conveyor reversing direction to rotate in the same direction as the endless loop conveyor of the second feeder.

2. In a feeder for discharging feed into one or more feed receiving means of an elongated feeding course, the combination comprising an elongated track extending longitudinally along said course and co-extensive therewith, a carriage mounted for travel along said track, drive means for reciprocatingly moving said carriage on said track, a pair of guide means longitudinally spaced from each other and disposed at opposite ends inside of said carriage, an endless loop conveyor member having an elongated top portion extending between said guides for receiving feed and with said conveyor member extending downwardly around said guides and extending inwardly beneath the said top portion, independent means selectively reciprocating said conveyor member about said guides in the same or opposite direction of movement of the carriage to carry feed for discharge at an end of said top portion into one of said receiving means, and the independent means being a first drive shaft connected to the drive means and normally continuously rotated in one direction by said motor, a second drive shaft spaced from the first shaft and adapted to be driven clockwise and counterclockwise, driven sprocket means secured to the first shaft, a second sprocket means disposed for free rotation on the second shaft, a first miter gear freely disposed for rotation on the second shaft in alignment with and secured to the sprocket means on the second shaft, drive means connecting the respective sprocket means to drive the sprocket means and miter gear on the second shaft from the driven means on the first shaft, a cross shaft follower keyed to the second shaft, at least one second gear secured to the cross shaft follower and meshed with the first miter gear to rotate the second drive shaft when the first miter gear is driven from the first drive shaft, an additional miter gear mounted for free rotation on the second shaft and meshing with the cross shaft follower and with the second gear, a pair of spaced pulleys mounted for free rotation on the second shaft and secured to the additional miter gear with one pulley being larger than the other pulley, a second pair of spaced pulleys secured to the first drive shaft in spaced relation with one pulley being of larger size than the other and the large pulley being in longitudinal alignment with the small pulley on the second drive shaft and the small pulley on the first drive shaft being in longitudinal alignment with the large pulley on the second drive shaft, a belt extending between the respective pair of pulleys on the first drive shaft and second drive shaft and normally in a loose position so that the pulleys on the second drive shaft are not rotated by the belts, means to independently tighten the belts on the pulleys to rotate the pulleys on the second drive shaft and thereby rotate the additional miter gear, the second gear, the cross shaft follower and the second drive shaft with the additional miter gear rotating the second drive shaft at a greater rpm than the first miter gear is tending to rotate the second drive shaft in the opposite direction when the belt on the set of pulleys having the small pulley on the second drive shaft is tightened to thereby rotate the second shaft in the same direction of rotation as the direction of rotation of the first drive shaft and when the belt on the set of pulleys having the large pulley on the second drive shaft is tightened to thereby tend to rotate the second shaft through the additional miter gear, second gear and cross shaft but at a slower rpm than the first miter gear is tending to drive the second drive shaft in the opposite direction to thereby effect driving of the second drive shaft by the first miter gear in a direction opposite to the first drive shaft.

* * * * *

UNITED STATES PATENT AND TRADEMARK OFFICE
CERTIFICATE OF CORRECTION

PATENT NO. : 4,119,193
DATED : October 10, 1978
INVENTOR(S) : KENNETH L. SMITH, ET AL It is certified that error appears in the above-identified patent and that said Letters Patent are hereby corrected as shown below:

Column 2, line 29, After "L3a" cancel "L3a" and insert ---L3b---;

Column 2, line 34, After "shuttle" cancel "zone";

Column 3, line 19, After "chains" insert ---19---;

Column 4, line 65, After "shaft 37" cancel "oopposite" and insert ---opposite---;

Column 6, line 3, After "will" cancel "rotae" and insert ---rotate---.

Signed and Sealed this

Sixth Day of February 1979

[SEAL]

Attest:

RUTH C. MASON
Attesting Officer

DONALD W. BANNER
Commissioner of Patents and Trademarks